US00PP17967P2

(12) United States Plant Patent
Vlielander

(10) Patent No.: US PP17,967 P2
(45) Date of Patent: Aug. 28, 2007

(54) ***KALANCHOE* PLANT NAMED 'FIVERANDA RED'**

(50) Latin Name: ***Kalanchoe guignardii*×*Kalanchoe blossfeldiana***
Varietal Denomination: Fiveranda Red

(75) Inventor: Ike Vlielander, De Lier (NL)

(73) Assignee: Fides B.V., De Lier (NL)

( * ) Notice: Subject to any disclaimer, the term of this patent is extended or adjusted under 35 U.S.C. 154(b) by 19 days.

(21) Appl. No.: 11/290,154

(22) Filed: Nov. 30, 2005

(51) Int. Cl.
*A01H 5/00* (2006.01)

(52) U.S. Cl. ..... Plt./341
(58) Field of Classification Search ..... Plt./335, Plt./341
See application file for complete search history.

*Primary Examiner*—Anne Marie Grunberg
*Assistant Examiner*—S. B. McCormick-Ewoldt

(57) ABSTRACT

A new cultivar of *Kalanchoe* plant named 'Fiveranda Red' that is characterized by red flowers, vigorous growth, strong branching, long flower life, short response time and a uniform crop.

1 Drawing Sheet

Botanical Classification: *Kalanchoe guignardii*×*Kalanchoe blossfeldiana.*
Variety Denomination: 'Fiveranda Red'.

BACKGROUND OF THE INVENTION

The present invention relates to a new and distinct cultivar of *Kalanchoe* plant botanically known as *Kalanchoe guignardii*×*Kalanchoe blossfeldiana* and hereinafter referred to by the cultivar name 'Fiveranda Red'.

The new cultivar is the product of a breeding program conducted by the inventor in a cultivated area of De Lier, The Netherlands. The objective of the breeding program is to develop new *Kalanchoe* cultivars with interesting and unique flower colors and shapes.

'Fiveranda Red' is a hybrid that originated from the induced hybridization of the female or seed parent *Kalanchoe guignardii* (unknown) (not patented) and the male or pollen parent *Kalanchoe blossfeldiana* 'FK 4170' (not patented). The cultivar 'Fiveranda Red' was selected by the inventor in 1999 as a single plant within the progeny of the stated cross in a controlled environment of De Lier, The Netherlands.

Asexual reproduction first occurred when terminal cuttings of the new cultivar 'Fiveranda Red' were propagated in 2000 in De Lier, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Kalanchoe* cultivar 'Fiveranda Red'. These traits in combination distinguish 'Fiveranda Red' as a new and distinct cultivar apart from other existing known varieties of *Kalanchoe.*

1. *Kalanchoe* 'Fiveranda Red' exhibits vigorous growth.
2. *Kalanchoe* 'Fiveranda Red' exhibits strong branching.
3. *Kalanchoe* 'Fiveranda Red' exhibits a long flower life.
4. *Kalanchoe* 'Fiveranda Red' exhibits a short response time.

5. *Kalanchoe* 'Fiveranda Red' exhibits red flowers.
6. *Kalanchoe* 'Fiveranda Red' exhibits a uniform crop.

The new cultivar 'Fiveranda Red' is distinguishable from the female parent *Kalanchoe guignardii* by the following characteristics:

1. 'Fiveranda Red' exhibits more vigorous growth than *Kalanchoe guignardi.*
2. 'Fiveranda Red' exhibits red flowers. The flowers of the female parent *Kalanchoe guignardii* are darker red.
3. 'Fiveranda Red' exhibits flowers that open more fully than *Kalanchoe guignardii.*

The new cultivar 'Fiveranda Red' is distinguishable from the male parent *Kalanchoe* 'FK 4170' by the following characteristics:

1. 'Fiveranda Red' is larger than 'FK 4170'.
2. 'Fiveranda Red' exhibits red flowers. The flowers of 'FK 4170' are white-pink.
3. 'Fiveranda Red' exhibits stronger branching.
4. 'Fiveranda Red' exhibits more vigorous growth.

The closest comparison cultivar is *Kalanchoe* 'Fiveranda Pink' (U.S. Plant Pat. No. 16,189). The new cultivar 'Fiveranda Red' is distinguishable from 'Fiveranda Pink' by the following characteristics:

1. 'Fiveranda Red' exhibits red flowers. The flowers of 'Fiveranda Pink' are pink.

BRIEF DESCRIPTION OF THE DRAWING

The accompanying photograph illustrates the distinguishing traits of *Kalanchoe* 'Fiveranda Red'. The plant in the photograph shows an overall view of a 18 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Kalanchoe* cultivar named 'Fiveranda Red'. Data was collected in De Lier, The Netherlands from 18 week glass greenhouse grown plants in 6 inch diameter containers. The time of year was Spring and the temperature was kept at 20° Centigrade during the day and night. The light level was natural outdoor light supplemented with artificial light below 10,000 lux. Photoperiodic treatments of 3 weeks of long days (more than 14 hours of light) followed by 8 weeks of short days (more than 14 hours of darkness) were used. No overhead watering was applied during the last 6 weeks. Color determinations are in accordance with The Royal Horticultural Society Colour Chart 2001 edition, except where general color terms of ordinary dictionary significance are used. The growing requirements are similar to the species. 'Fiveranda Red' has not been tested under all possible conditions and phenotype differences may be observed with variations in environmental, climatic, and cultural conditions, however, without any variance in genotype.

Botanical classification: *Kalanchoe* 'Fiveranda Red'.
Use: Ornamental Annual.
Parentage: 'Fiveranda Red' is a hybrid plant that resulted from the induced hybridization of the following parent plants:
*Female parent.*—*Kalanchoe guignardii.*
*Male parent.*—*Kalanchoe blossfeldiana* 'FK 4170'.
Vigor: Very Strong.
Growth habit: Upright and uniform.
Plant shape: Rounded, Triangular.
Suitable container size: 6 inch diameter container.
Height: 29 cm. in height.
Width: 38 cm. in width.
Low temperature tolerance: 16 degrees Centigrade.
High temperature tolerance: 35 degrees Centigrade.
Propagation: Terminal cuttings.
Time to initiate roots: 10–14 days to initiate roots as 21 degrees Centigrade.
Time to produce a rooted cutting or liner: 15–18 days at 21 degrees Centigrade.
Crop time: 11–14 weeks are required to produce a finished flowering plant.
Root system: Fine and fibrous.
Stem:
*Branching habit.*—Freely branching with shoots at every node.
*Average number of lateral branches.*—10–12.
*Pinching.*—Not Required.
*Lateral branch diameter.*—9–12 mm. in diameter.
*Lateral branch length.*—17–22 cm. in length.
*Lateral branch strength.*—Very strong.
*Stem diameter.*—18–22 mm. in diameter.
*Stem color.*—147A.
*Stem shape.*—Straight.
*Pubescence.*—Absent.
*Internode length.*—3–5 cm. between nodes.
*Aspect.*—Upright.
Foliage:
*Texture.*—Both sides glabrous, coriaceous, succulent.
*Leaf arrangement.*—Opposite.
*Compound or single.*—Single.
*Quantity of leaves per lateral branch.*—8–13.
*Leaf shape.*—Ovate/Elliptic.
*Leaf apex.*—Acute to Obtuse.
*Leaf base.*—Acute.
*Leaf length.*—17 cm. in length.
*Leaf width.*—12 cm. in width.
*Pubescence.*—Absent.
*Leaf margin.*—Crenate.
*Young leaf color* (*lower surface*).—147B.
*Young leaf color* (*upper surface*).—147A.
*Mature leaf color* (*lower surface*).—147B.
*Mature leaf color* (*upper surface*).—147A.
*Vein color* (*lower surface*).—147B.
*Vein color* (*upper surface*).—147A to 147B.
*Venation pattern.*—Pinnate.
*Leaf attachment.*—Petiolate.
*Petiole dimensions.*—20 mm. in length and 6–8 mm. in width.
*Petiole color upper side.*—147A to 147B.
*Petiole color lower side.*—147A to 147B.
Flower:
*Inflorescence arrangement.*—Single flowers arranged in racemes forming an umbel.
*Flowering habit.*—Continuous.
*Quantity of flowers per lateral stem.*—Over 40.
*Quantity of flower buds per lateral stem.*—Over 40.
*Quantity of flowers and buds per plant.*—Over 250.
*Natural flowering season.*—November/December in the Northern Hemisphere.
*Time to flower.*—10–12 weeks.
*Fragrance.*—None.
*Flower bud length.*—10 mm. in length.
*Flower bud diameter.*—2 mm. in diameter.
*Flower bud shape.*—Oblong, tubular and ovoid.
*Bud color.*—55C to 55D.
*Rate of bud opening.*—1 day.
*Flower aspect.*—Cupped/Raceme/Bell.
*Flower shape.*—Petals fused at base to form a bell shaped corolla.
*Flower dimensions.*—16 mm. in diameter and 14 mm. in height.
*Flower longevity.*—Approximately 17 days.
*Petal appearance.*—Shiny.
*Petal texture.*—Glabrous.
*Number of petals.*—4.
*Fused or unfused.*—Unfused.
*Petal appearance.*—Flat to partially upright.
*Petal shape.*—Ovate.
*Petal margin.*—Entire.
*Petal apex.*—Obtuse.
*Petal dimensions.*—7 mm. in length and 4 mm. in width.
*Petal color when opening* (*upper side*).—46B.
*Petal color when opening* (*under side*).—46D.
*Petal color fully opened* (*upper side*).—46B.
*Petal color fully opened* (*under side*).—46D.
*Petal color fading to.*—46C.
*Self-cleaning or persistent.*—Persistent.
Sepals:
*Number of sepals.*—Four.
*Sepal Aspect.*—Upright, rigid.
*Sepal shape.*—Oblong/Pointed.
*Sepal margin.*—Entire.
*Sepal apex.*—Acute.
*Sepal base.*—Rounded.
*Sepal surface.*—Smooth, shiny.
*Sepal dimensions.*—6 mm in length and 2 mm. in width.
*Sepal color* (*upper side*).—138D.
*Sepal color* (*under side*).—138D.
Calyx:
*Calyx shape.*—Funnel.
*Calyx dimensions.*—16 mm in length and 4 mm in diameter.

Peduncle:

*Peduncle dimensions.*—7 mm. in length and 1 mm. in diameter.

*Peduncle aspect.*—Rigid.

*Peduncle texture.*—Smooth.

*Peduncle color.*—138B.

*Peduncle strength.*—Strong.

Reproduction organs:

*Stamen number.*—8.

*Anther shape.*—Flat, Elliptic.

*Anther dimensions.*—0.3 mm. in length and 0.3 mm. in width.

*Anther color.*—150D.

*Amount of pollen.*—Low.

*Pollen color.*—12A.

*Pistil number.*—4.

*Pistil dimensions.*—1 mm. in length.

*Stigma shape.*—Flat.

*Stigma color.*—8D.

*Style length.*—10 mm.

*Style color.*—138D.

*Ovary color.*—138D.

Seed:

*Seed length.*—0.1 mm.

*Seed diameter.*—0.05 mm.

*Seed color.*—166C.

*Quantity of seeds.*—0–500 per plant.

Disease and insect resistance: No disease problems observed, slight susceptibilty to aphids.

It is claimed:

1. A new and distinct variety of *Kalanchoe* plant named 'Fiveranda Red' as described and illustrated.

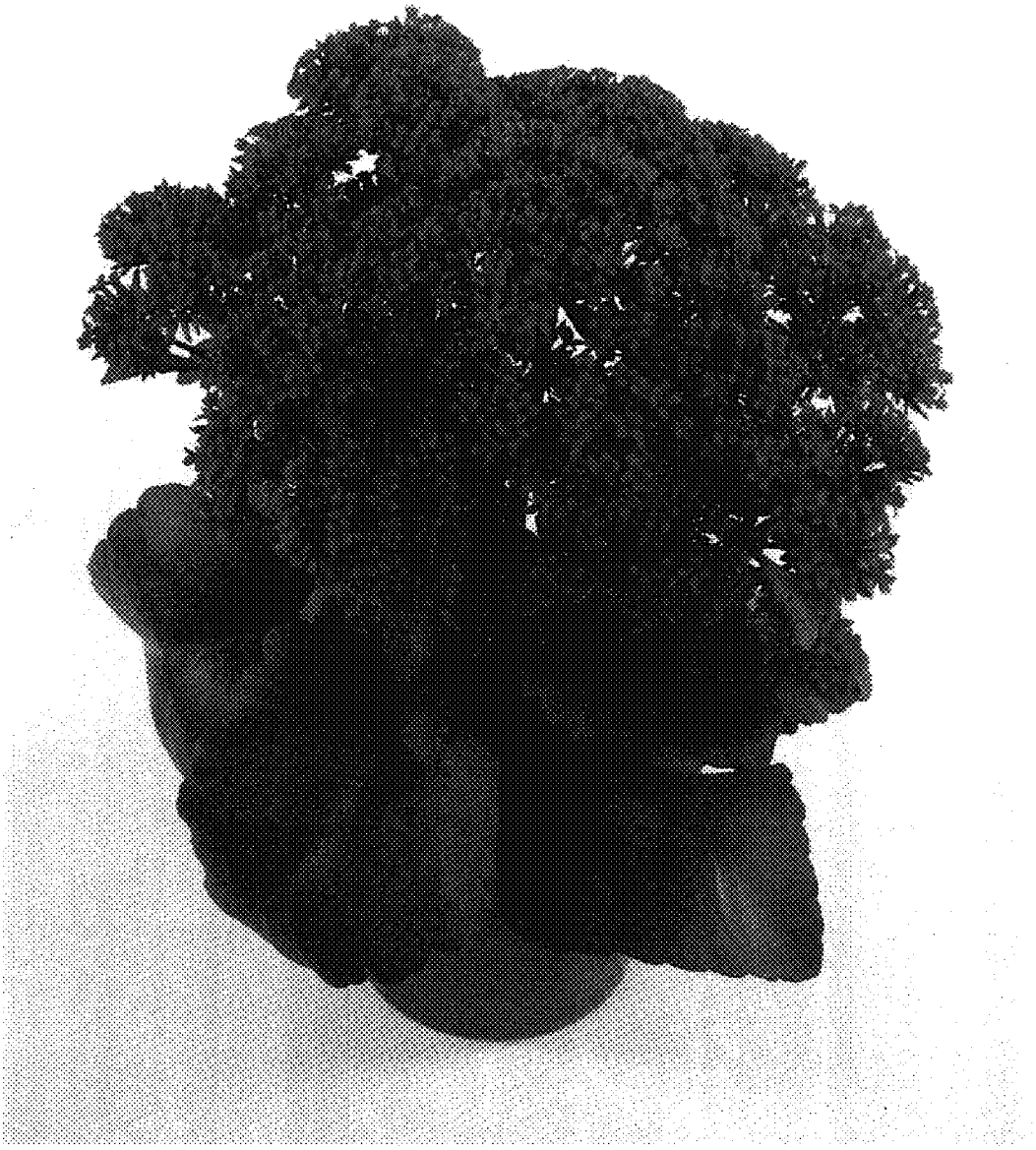

* * * * *